(12) United States Patent
Vigano' et al.

(10) Patent No.: US 7,671,197 B2
(45) Date of Patent: Mar. 2, 2010

(54) PROCESS FOR THE PURIFICATION OF MELOXICAM

(75) Inventors: Enrico Vigano', Lurago D'Erba (IT); Ernesto Landonio, Rescaldina (IT)

(73) Assignee: A.M.S.A. Anonima Materie Sintetiche E Affini S.p.A., Milan (IT)

( * ) Notice: Subject to any disclaimer, the term of this patent is extended or adjusted under 35 U.S.C. 154(b) by 565 days.

(21) Appl. No.: 11/249,019

(22) Filed: Oct. 11, 2005

(65) Prior Publication Data

US 2006/0116514 A1 Jun. 1, 2006

(30) Foreign Application Priority Data

Oct. 11, 2004 (IT) .......................... MI2004A1918

(51) Int. Cl.
*C07D 417/00* (2006.01)
(52) U.S. Cl. ...................................... 544/49
(58) Field of Classification Search .................... 544/49
See application file for complete search history.

(56) References Cited

U.S. PATENT DOCUMENTS 4,233,299 A  11/1980  Trummlitz et al.

2003/0109701 A1  6/2003  Coppi et al.

OTHER PUBLICATIONS

Ochoa, L. et al. (2003) "improved procedure for the preparation of 4-hydroxy-2-methyl-N-(5-methyl-2-thiazolyl)-2H-1,2-benzothiazine-3-carboxamide, 1, 1-dioxide (meloxicam)" Abstract, Chemical Abstracts Service, Database accession No. 2003:711263.
Liu et al. (2002) Abstract from CN 1342650 "Purification comprise add crude formamide".
European Search Report from corresponding European patent application serial No. EP 05109383.9-2117, Oct. 2, 2006.
Luger, P. (1996) "Structure and physicochemical properties of meloxicam, a new NSAID" European Journal of Pharmaceutical Sciences 4:175-187.

*Primary Examiner*—Taylor Victor Oh
(74) *Attorney, Agent, or Firm*—Knobbe, Martens, Olson & Bear, LLP

(57) ABSTRACT

The present invention relates to a process for the purification of meloxicam and in particular of the impurity composed of 4-hydroxy-2-methyl-N-ethyl-N'-(5-methyl-2-thiazolyl)-2H-1,2-benzothiazine-3-carboxamide-1,1-dioxide and to meloxicam containing a quantity of less than 0.05% of the above-mentioned impurity ("ethylamide").

29 Claims, No Drawings

PROCESS FOR THE PURIFICATION OF MELOXICAM

FIELD OF THE INVENTION

The present invention relates to a process for the purification of meloxicam and in particular of the impurity composed of 4-hydroxy-2-methyl-N-ethyl-N'-(5-methyl-2-thiazolyl)-2H-1,2-benzothiazine-3-carboxamide-1,1-dioxide and to meloxicam containing a quantity of less than 0.05% of the above-mentioned impurity ("ethylamide").

STATE OF THE ART

Non Steroidal Anti-Inflammatory Drugs (NSAID) are widely used for the long-term treatments of chronic diseases of rheumatic origin such as rheumatoid arthritis, osteoarthritis, ankylosing spondylitis.

However, NSAID also present considerable side effects partly due to the differences in the respective chemical and physical properties such as for example the ionization constants, ($pK_a$), solubility, partition coefficient, which determine their distribution in the body.

Most NSAID are weak acids with $pK_a$ values between 3 and 5, in addition the partition coefficients expressed as logP of the NSAID give an idea of their lipophilicity and relative ability to pass through the cellular membrane and thus enter the cell. The target enzyme of NSAID is Cyclooxygenase (COX), in other words the enzyme that limits the synthesis of prostaglandin.

Meloxicam is a recent NSAID belonging to the class of acid enols. It has been chosen for pharmaceutical development because in pharmacological tests it has proven to be highly efficacious as concerns anti-arthritic activity; moreover it presents a wider spectrum of anti-inflammatory activity associated with less irritation of the gastric tissue if administered systemically or locally (dermic, rectal, ocular), if administered topically, in comparison with less recent NSAID.

With the discovery that the COX enzyme exists in 2 isoforms, respectively COX-1 (responsible for physiological regulation) and COX-2 (induced by the inflammatory mediators in pathological conditions), it has been demonstrated that meloxicam is a powerful inhibitor of the form COX-2 (P. Luger et al European Journal of Pharmaceutical Science 4 (1996) 175-187).

Meloxicam exists in different polymorphous forms, the most important of which are: polymorphous form (I) that is the enolic form which is used in the preparation of pharmaceutical formulations and is characterised by the following formula

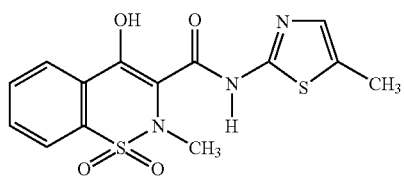

and the zwitterionic polymorphous form characterised in particular by the following formulae in equilibrium with each other.

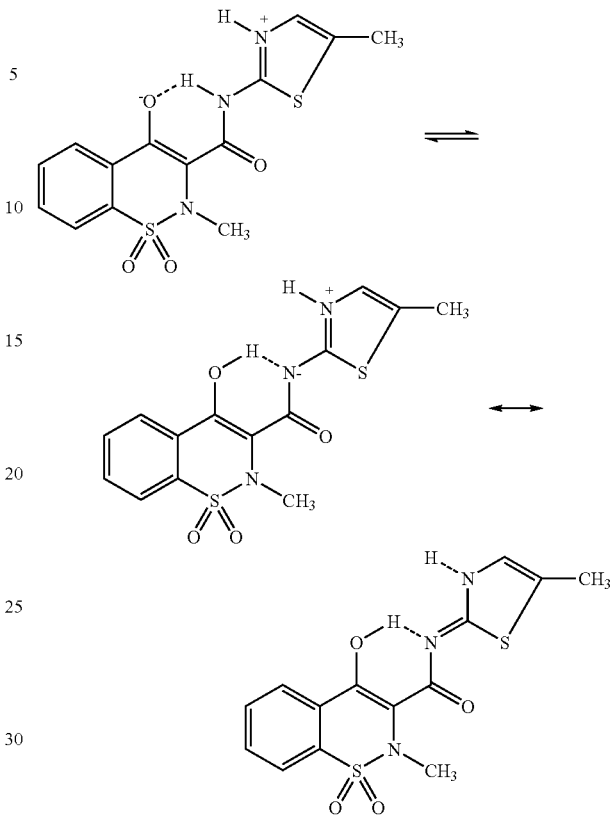

The patent application US2003/0109701 describes further polymorphous forms of meloxicam (II), (III) and (V) which however cannot be used in pharmaceutical preparations and which differ both from the polymorphous form (I) and from each other in the Raman spectra, the IR and the X ray difractograms.

These polymorphous forms easily convertible into form (I) are prepared with specific processes, of which the critical parameters that favour the formation of a specific form with respect to others are:

the type of solvent (water, for form (II) and (V), water and small amounts of xylene between 5 and 10% by weight on weight of meloxicam for form (III)), the temperature (40-45° C. for form (V)), 45-50° C. for forms (II) and (III), the water volume/weight of meloxicam ratio (between 20 and 25 for form (III), less than 30 for form (V) and between 30 and 35 for form (II)).

U.S. Pat. No. 4,233,299 describes the synthesis of that active principle which in particular requires the reaction between a methylic or ethylic ester of 4-hydroxy-2-methyl-2H-1,2-benzothiazine-3-carboxylate-1,1-dioxide with 2-amino-5-methyl-thiazole, the product thus obtained is in crude form.

The processes of isolation and purification to form (I) contemplated the crystallisation of meloxicam in crude form from an apolar solvent such as methylene chloride as described in the above-mentioned U.S. Pat. No. 4,233,299 or by crystallisation from a polar aprotic solvent such as tetrahydrofurane as described in the above-mentioned article by P. Luger et al.

The best results are obtained by dissolving meloxicam in an alcoholic solvent or in water, transforming it by treatment with bases such as alkaline alcolates, alkaline hydroxides or ammonia into the corresponding enolate which, after the macroscopic impurities have been eliminated by respective filtration, is then transformed into meloxicam by acidification. The precipitate obtained after acidification is isolated from the reaction mixture by drying.

Even though this process represents an improvement with respect to the first crystallisation treatments since it allows the elimination to acceptable values of the following pollutants: 2-amino-5-methyl-thiazole and ethyl 4-hydroxy-2-methyl-2H-1,2-benzothiazine-1,1-dioxide-3-carboxylate, with this method it is not possible to lower below 0.10% the content of 4-hydroxy-2-methyl-N-ethyl-N'-(5-methyl-2-thiazolyl)-2H-1,2-benzothiazine-3-carboxamide-1,1-dioxide, which is also formed during the above-mentioned reaction of meloxicam formation.

For the pharmacopeia this sub-product must be present in meloxicam in quantities lower than or equal to 0.05%.

The need was therefore felt to have a process for purifying meloxicam which would allow the above-mentioned impurity to be reduced to acceptable values for the Pharmacopeia.

SUMMARY OF THE INVENTION

The Applicant has surprisingly found a process for purifying meloxicam which allows the above-mentioned impurity to be reduced to values lower than 0.05% and in particular to values between 0.009 and 0.026%.

With the process of the invention it is also possible to reduce further the other impurities to values less than 0.01% in weight, and to remove the stained sub-products in the final purification solvent.

In particular the process object of the present invention comprises the following steps:
a) the meloxicam is treated in crude form with an alcohol solution of an alkaline alcoholate at a temperature comprised between 25 and 35° C.
b) the solution obtained in step (a) is acidified to a pH between 1.5 and 4.0 and the precipitated product composed of meloxicam is filtered,
c) the wet filtered product obtained from the previous step is crushed in a polar aprotic solvent and the product of the crushing is isolated by means of filtration and drying.

DETAILED DESCRIPTION OF THE INVENTION

In the present description the definition of ambient temperature means a temperature between 20 and 25° C.

Step (a) is preferably carried out using as alcohol an alcohol having 1 to 5 carbon atoms and even more preferably methanol is used. The alkaline alcoholate always used in step (a) is an alcoholate having 1 to 5 carbon atoms, in which the cation is preferably chosen between $Na^+$ and $K^+$ and even more preferably it is sodium methylate.

The pH interval used in step (b) is critical because the Applicant has pointed out that, if it is acidified to pH values higher than 4, there may be incomplete precipitation of meloxicam and therefore problems of title and ash, since the meloxicam is present in the form of a salt, whereas when operating at pH<1.5 the final purification performed with step (c) of the process according to the present invention loses its effectiveness as shown in the comparative examples listed below.

According to a particularly preferred embodiment of the process in the present invention, the pH of step (b) is between 2 and 4.

The acid used in step (b) is preferably chosen from hydrochloric acid, sulfuric acid, phosphoric acid, even more preferably it is concentrated hydrochloric acid.

In step (c) the crushing in a polar aprotic solvent preferably comprises the following operative modes:
c-1) the meloxicam is crushed at ambient temperature,
c-2) the mixture is heated to the boiling point of the solvent,
c-3) the mixture is kept at the above-mentioned temperature for about 1 hour and is then cooled to ambient temperature.

In step (c) the polar aprotic solvent is preferably chosen from a ketone, an ether or an ester and respective mixtures.

The ether used in step (c) is preferably chosen between glyme and diglyme, and respective mixtures, even more preferably it is glyme.

In the class of esters the preferred ones belong to the class of acetic acid esters with linear or branched alcohols having 1 to 5 carbon atoms.

Even more preferably ethyl acetate is used.

Preferably in the process object of the present invention the polar aprotic solvent used in step (c) is a ketone preferably chosen in the class composed of acetone, methylethylketone, methylisobutylketone.

According to a particularly preferred embodiment of the process object of the present invention, step (c) is carried out using acetone as a solvent.

According to another particularly preferred embodiment, the process object of the present invention also contemplates washing or crushing in water of the acidified meloxicam arriving from step (b) in order to eliminate from the meloxicam the inorganic salts which are inevitably formed in this step. This washing or crushing may be performed either on the wet filtered product coming from step (b) or during step (c), after crushing with a polar aprotic solvent and before isolation of the end product.

The purified product obtained with the process object of the present invention is the already known polymorphous form (I).

The crude meloxicam used in the present invention is obtained by making the 4-hydroxy-2-methyl-2H-1,2-benzothiazine-3-carboxylate of ethyl-1,1-dioxide react with 2-amino-5-methyl-thiazole in xylene according to the following scheme:

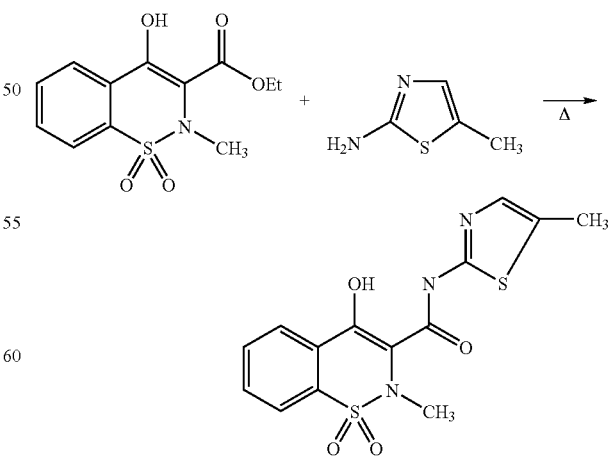

The reaction is carried out under reflux in the presence of molecular sieves 4 Å or 5 Å suited to adsorb the ethanol which is formed. The crude meloxicam is isolated by filtration and used wet in the purification process in the present invention.

The Applicant has also found that with the process of the present invention it is possible to lower the impurity composed of ethylamide to values lower than 0.05% starting from crude meloxicam coming from the above-mentioned reaction containing the above-mentioned impurity up to values of about 1%.

A further advantage of the process object of the present invention lies in the use of non-toxic solvents, thus avoiding the use of toxic solvents such as chlorinated solvents and dimethylformamide, which are the customary crystallisation solvents for meloxicam.

Some examples of the process object of the present invention are given for the purpose of illustration without limitation.

EXAMPLE 1

Process for Preparing Crude Meloxicam

In a 6 liter round-bottom flask, in a nitrogen flow, are placed respectively 226.64 g (0.80 mol) of 4-hydroxy-2-methyl-2H-1,2-benzothiazine-3-carboxylate of ethyl-1,1-dioxide and 91.36 g (0.80 mol) of 2-amino-5-methyl-thiazole and 3.6 l of xylene.

The suspension is heated under reflux (139-140° C.), passing the condensate on a bed of molecular sieves 4 Å. Initially a dark brown solution is obtained and then, as the reaction proceeds, the reaction product is crystallised in the form of a yellow-green solid.

It is kept under reflux until completion of the reaction (32-37 hours).

When the reaction is completed it is cooled to a temperature comprised between 20 and 25° C. in at least 2 hours. The crude product is filtered and washed with xylol and acetone.

279.34 g of wet yellow-greenish crude product are obtained, the equivalent of 260.0 g of dry product.

Theoretical yield 281.12 g
RDT=92.48%.

The crude meloxicam thus obtained has a content of the impurity composed of ethylamide amounting to 0.707% assessed with HPLC using the "Related substances" method given in the monographic report of the British Pharmacopoeia 2002.

Repeating example 1, products are obtained that contain the above-mentioned impurity in variable quantities between 0.230 and 0.782%.

EXAMPLE 2

Process for Purifying Meloxicam i) Preparation of meloxicam in wet form (step (a) and (b) of the process)

In a 2 liter round-bottom flask, in a nitrogen flow, are suspended at ambient temperature 100 g of crude meloxicam obtained in example 1 (containing the impurity composed of ethylamide amounting to 0.707%), in 1 l of methanol. In about 10 minutes 55 ml of a solution of 30% sodium methylate in methanol are added. The temperature rises spontaneously due to the exothermic character of the salification reaction. 5 g of activated carbon are added to the dark solution obtained. The solution is clarified perfectly by filtration on a panel of dicalite. The panel is washed with 200 ml of methanol and the washing waters are added to the filtered principal solution. The meloxicam is precipitated by adding concentrated hydrochloric acid in about 1 hour until a pH value of 2.3-2.4 is reached (24 ml).

The suspension is then left stirring for about 1 hour, the product obtained is filtered and washed with 100 ml of water, and finally it is crushed in a liter of water. The product if finally filtered and analysed with HPLC.

The ethylamide content of this wet product is 0.21%.

ii) Final purification (step(c)) of the process 285,1 g of wet product obtained in (i) are crushed in 1250 ml of acetone. The yellow suspension thus obtained is refluxed (56-58° C.) and is kept at that temperature for about 1 hour. It is cooled to ambient temperature, filtered and washed with acetone.

246.35 g of bright yellow wet product are obtained.

The product is dried in the vacuum oven at 55-65° C. for about 8 hours.

243.35 g of finished dry meloxicam are obtained with an impurity content checked by HPLC analysis amounting to 0.022%.

Example 2 is repeated, acidifying at different pH values and also using different crude meloxicam products containing different initial quantities of ethylamide. The results are listed below in table form, starting from the same crude product.

TABLE 1

| EXAMPLE | Ethylamide content in crude meloxicam (A %) | pH of precipitation | Ethylamide content after salification and acidification | Ethylamide content after final crushing in acetone |
|---|---|---|---|---|
| 2A | 0.390 | 3.70 | 0.176 | 0.023 |
| 2B | 0.390 | 2.23 | 0.194 | 0.020 |
| 2C | 0.390 | 1.97 | 0.187 | 0.026 |
| 2D | 0.390 | 1.52 | 0.199 | 0.052 |
| 2E | 0.390 | 1.12 | 0.137 | 0.114 |

As may be seen from the above data, the acidification pH is a critical parameter for the subsequent purification by crushing in a polar aprotic solvent.

EXAMPLE 3

The process described in example 2 (ii) is repeated, using 10 g of meloxicam resulting from acidification and which contains ethylamide in values of 0.165%, using solvents other than acetone.

The results obtained are listed below in table 2.

TABLE 2

| Example | solvent | Volume of solvent (ml) | boiling T (° C.) | (%) of ethylamide |
|---|---|---|---|---|
| 3A | Methanol | 50 | 64 | 0.126 |
| 3B | isopropanol | 100 | 80 | 0.161 |
| 3C | Toluene | 50 | 110 | 0.164 |
| 3D | Glyme | 50 | 85 | 0.016 |
| 3E | Methylethylketone | 50 | 80 | 0.012 |
| 3F | Methylisobutylketone | 50 | 127 | 0.015 |
| 3F | Ethyl acetate | 50 | 76 | 0.021 |

As may be seen from the data recited in Table 2, only the polar aprotic solvents allow the elimination of ethylamide to values lower than those required by the Pharmacopoeia.

The invention claimed is:

1. Process for the purification of meloxicam comprising the following steps:
   a) the meloxicam is treated in crude form with an alcohol solution of an alkaline alcoholate at a temperature between 25 and 35° C.,
   b) the solution obtained in step (a) is acidified to a pH between 1.5 and 4.0 and the precipitated product composed of meloxicam is filtered,
   c) the wet filtered product obtained from the previous step is crushed in a polar aprotic solvent according to the following sub-steps:
      1) the meloxicam is crushed at ambient temperature,
      2) the mixture is heated to the boiling point of the solvent,
      3) the mixture is kept at the above-mentioned temperature for about 1 hour and is then cooled to ambient temperature; and
   the product of the crushing is isolated by means of filtration and drying.

2. Process according to claim 1, wherein the step (a) is carried out using as alcohol an alcohol having 1 to 5 carbon atoms.

3. Process according to claim 2, wherein the alcohol is methanol.

4. Process according to claim 1, wherein the alkaline alcoholate used in step (a) is an alcoholate having 1 to 5 carbon atoms in which the cation is chosen between Na+ and K+.

5. Process according to claim 4, wherein said alkaline metal alcoholate is sodium alcoholate.

6. Process according to claim 1, wherein the pH of step (b) is between 2 and 4.

7. Process according to claim 6, wherein the mineral acid is chosen from hydrochloric acid, sulfuric acid, phosphoric acid.

8. Process according to claim 7, wherein said mineral acid is concentrated hydrochloric acid.

9. Process according to claim 1, wherein in step (c) the polar aprotic solvent is chosen from a ketone, an ether or an ester and respective mixtures.

10. Process according to claim 9, wherein the ether used in step (c) is chosen between glyme and diglyme, and respective mixtures.

11. Process according to claim 10, wherein said ether is glyme.

12. Process according to claim 9, wherein the ester is chosen in the class of acetic acid esters with linear or branched alcohols having 1 to 5 carbon atoms.

13. Process according to claim 12, wherein ethyl acetate is used.

14. Process according to claim 9, wherein in step (c) the polar aprotic solvent is a ketone.

15. Process according to claim 14, wherein the ketone is chosen in the class composed of acetone, methylethylketone, methylisobutylketone.

16. Process according to claim 15, wherein the ketone is acetone.

17. Process according to claim 1, wherein in step (c) the polar aprotic solvent is chosen from a ketone, an ether or an ester and respective mixtures.

18. Process according to claim 17, wherein the ether used in step (c) is chosen between glyme and diglyme, and respective mixtures.

19. Process according to claim 18, wherein said ether is glyme.

20. Process according to claim 17, wherein the ester is chosen in the class of acetic acid esters with linear or branched alcohols having 1 to 5 carbon atoms.

21. Process according to claim 20, wherein ethyl acetate is used.

22. Process according to claim 17, wherein in step (c) the polar aprotic solvent is a ketone.

23. Process according to claim 22, wherein the ketone is chosen in the class composed of acetone, methylethylketone, methylisobutylketone.

24. Process according to claim 23, wherein the ketone is acetone.

25. Process according to claim 1, wherein the meloxicam obtained after acidification is washed or crushed in water in order to eliminate the inorganic salts which are formed in this step.

26. Process according to claim 25, wherein said washing or crushing in water is carried out after step (b).

27. Process according to claim 25, wherein said washing or crushing is carried out during step (c) after crushing with polar aprotic solvent and before isolation of the end product.

28. The composition according to claim 27, wherein said 4-hydroxy-2-methyl-N-ethyl-N'-(5-methyl-2-thiazolyl)-2H-1,2-benzothiazine-3-carboxamide is in an amount between 0.009 and 0.026%.

29. A composition consisting essentially of Meloxicam, wherein said composition comprises 4-hydroxy-2-methyl-N-ethyl-N'-(5-methyl-2-thiazolyl)-2H-1,2-benzothiazine-3-carboxamide, said 4-hydroxy-2-methyl-N-ethyl-N'-(5-methyl-2-thiazolyl)-2H-1,2-benzothiazine-3-carboxamide being present in an amount more than 0% and lower than or equal to 0.05%.

* * * * *